US006569408B1

(12) United States Patent
Yue et al.

(10) Patent No.: US 6,569,408 B1
(45) Date of Patent: *May 27, 2003

(54) COMPOSITIONS COMPRISING ORGANOSILOXANE RESINS FOR DELIVERING ORAL CARE SUBSTANCES

(75) Inventors: Jiang Yue, West Chester, OH (US); Mark Matthew Crisanti, Cincinnati, OH (US); Satyanarayana Majeti, Cincinnati, OH (US); Steven Carl Burgess, Sharonville, OH (US); Elizabeth Ann Reno, Fairfield, OH (US); Li Li, West Chester, OH (US); Shekhar Mitra, Indian Hill, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/019,038

(22) PCT Filed: Jun. 9, 2000

(86) PCT No.: PCT/US00/15890
§ 371 (c)(1),
(2), (4) Date: Dec. 20, 2001

(87) PCT Pub. No.: WO01/01939

PCT Pub. Date: Jan. 11, 2001

(30) Foreign Application Priority Data

Jul. 2, 2000 (WO) .............................. PCT/US99/15130

(51) Int. Cl.⁷ .......................... A61K 7/16; A61K 6/08; A61C 5/00; C09K 3/00
(52) U.S. Cl. .................. 424/49; 433/217.1; 433/228.1; 523/116; 523/118
(58) Field of Search ............... 424/49–58; 433/215, 433/216, 217.1, 228.1; 523/116; 106/701

(56) References Cited

U.S. PATENT DOCUMENTS

| | | | | |
|---|---|---|---|---|
| 4,032,627 A | * | 6/1977 | Suchan et al. | 424/49 |
| 4,141,144 A | * | 2/1979 | Lustgarten | 32/15 |
| 4,150,485 A | * | 4/1979 | Lee et al. | 32/15 |
| 5,338,773 A | * | 8/1994 | Lu et al. | 523/116 |
| 5,401,528 A | | 3/1995 | Schmidt | |
| 5,425,953 A | | 6/1995 | Sintov et al. | |
| 5,427,770 A | | 6/1995 | Viccaro et al. | |
| 5,438,076 A | | 8/1995 | Friedman et al. | |
| 5,688,492 A | * | 11/1997 | Galley et al. | 424/49 |
| 5,759,523 A | * | 6/1998 | Hughes | 424/53 |
| 5,856,282 A | * | 1/1999 | Hughes | 510/117 |
| 5,965,632 A | * | 10/1999 | Orlowski et al. | 523/116 |
| 6,008,171 A | * | 12/1999 | Hughes | 510/117 |
| 6,019,962 A | * | 2/2000 | Rabe et al. | 424/64 |
| 6,024,891 A | * | 2/2000 | Hughes | 252/186.31 |
| 6,071,503 A | * | 6/2000 | Drechsler et al. | 424/64 |
| 6,074,654 A | * | 6/2000 | Drechsler et al. | 424/401 |
| 6,083,421 A | * | 7/2000 | Huang et al. | 252/186.28 |
| 6,123,950 A | * | 9/2000 | Hughes | 424/401 |
| 6,139,823 A | * | 10/2000 | Drechsler et al. | 424/64 |
| 6,340,466 B1 | * | 1/2002 | Drechsler et al. | 424/401 |
| 6,406,683 B1 | * | 6/2002 | Drechsler et al. | 424/64 |

FOREIGN PATENT DOCUMENTS

WO    WO 98/55079    12/1998

* cited by examiner

Primary Examiner—Shep K. Rose
(74) Attorney, Agent, or Firm—Evelyn L. Hiland; Betty J. Zea

(57) ABSTRACT

Disclosed is a composition for delivering an oral care substance to the oral cavity, comprising: (a) an organosiloxane resin; (b) a volatile carrier capable of solubilizing the organosiloxane resin; (c) a rheology modifier; and (d) at least one oral care substance. The present invention is also directed to such compositions comprising: (a) an organosiloxane resin; (b) a fluid diorganopolysiloxane polymer; (c) a volatile carrier capable of solubilizing the organosiloxane resin and the fluid diorganopolysiloxane polymer; (d) a rheology modifier; and (e) at least one oral care substance. Further disclosed is a method of using these compositions

25 Claims, No Drawings

COMPOSITIONS COMPRISING ORGANOSILOXANE RESINS FOR DELIVERING ORAL CARE SUBSTANCES

FIELD

The present invention relates to compositions for delivering oral care substances to the surfaces of the teeth. The composition forms a film on the surface to which it has been applied. Said film contains oral care substances for enhancing the appearance of the teeth. These films may also provide sustained release of certain oral care substances from the film for prolonged therapeutic and, or prophylactic benefits. More specifically, the present invention relates to compositions comprising organosiloxane resins for delivering oral care substances to the tooth enamel. In addition, it is believed that the compositions herein may further provide sustained release benefits to other oral surfaces, such as the gingival and mucosal tissues, as well as to the surfaces of the teeth.

BACKGROUND

Oral care products by which various oral care substances or actives can be delivered to the soft and hard tissues of the oral cavity have previously been known. Examples of such oral care products include, for example, brushing aids such as dentifrice products for delivery of anti-caries actives such as fluoride or other actives for the reduction of the bacteria that lead to the formation of plaque, and mouthwashes containing breath freshening actives and/or anti-bacterial actives. In addition, bleaching agents such as peroxide that can be applied directly to the surfaces of the teeth, i.e., to the tooth enamel, have been developed.

However, it has been found that such conventional product forms typically do not provide substantivity sufficient to maintain actives on the hard and soft oral tissues for a period of time sufficient to enhance or prolong the therapeutic, prophylactic, and/or cosmetic benefits provided by the actives. Neither have such conventional product forms been able to provide sustained delivery of oral care actives, without periodic reapplication at relatively short time intervals, or without a special delivery device or containment means such as a mouthpiece.

Attempts have previously been made to enhance the substantivity of whitening bleaches, bactericides, and other active components of oral care products. See, e.g., U.S. Pat. No. 5,425,953 to Sintov et al. on Jun. 20, 1995, in which a film forming, water-soluble cellulosic polymer is used to deliver a bleaching agent to the teeth; U.S. Pat. No. 5,438,076 to Friedman et al., in which liquid methacrylate acid copolymer compositions are used to deliver a bacteriocidal pharmacological agent; and International Patent Appln. No. PCT/CN97/00 to Huang, published on Jul. 24, 1997, disclosing a film-coating composition comprising cellulose and polyvinyl acetal, coumarone-indene resin, or shellace as a film former to deliver bleaches to the tooth enamel.

However, the above systems are water-soluble, i.e., they are readily dissolved by saliva, generally within about 1–3 hours after application. Therefore, their degree of durability is low, and they cannot provide long-term delivery of the active ingredient that is present in the composition. In addition, their water-soluble nature precludes them from being used with oral care actives that would be unstable in water-based films. Sodium percarbonate is one example of such an active; it would be unstable in the high pH environment of an aqueous-based film.

In order to provide an applied composition with a relatively higher degree of durability, the use of protective coatings that are applied to the teeth has been described. See, U.S. Pat. No. 5,401,528, to Schmidt on Mar. 18, 1995, in which organically modified silicic acid polycondensates are deposited on the teeth, then polymerized in-situ by curing, to coat the teeth in order to protect them from plaque deposits. This system is not a true delivery system by which an active ingredient is released over time; instead, it provides a barrier by which the deleterious effect of plaque-causing bacteria may be diminished.

Although such a barrier coating may offer a benefit in terms of enhanced durability, it requires the use of special equipment and complex application; thus, it cannot be performed at home and cannot be used for self-treatment.

Therefore, it can be seen that none of these previous developments can offer the combination of both long-term delivery of an oral care substance or active ingredient and the convenience of discrete self-treatment and home use. Based on the foregoing, there is a need for a convenient delivery system for various oral care substances in which the substantivity of the active ingredients is enhanced. None of the existing art provides all of the advantages and benefits of the present invention.

SUMMARY

The present invention is directed to compositions for delivering oral care substances to the oral cavity, comprising: (a) an organosiloxane resin; (b) a volatile carrier capable of solubilizing the organosiloxane resin; (c) a rheology modifier; and (d) at least one oral care substance. The present invention is also directed to such compositions comprising: (a) an organosiloxane resin; (b) a fluid diorganopolysiloxane-based polymer; (c) a volatile carrier capable of solubilizing the organosiloxane resin and the fluid diorganopolysiloxane-based polymer; (d) a rheology modifier; and (e) at least one oral care substance. The present invention further is directed to a method of using these compositions.

These and other features, aspects, and advantages of the invention will become evident to those skilled in the art from a reading of the present disclosure.

DETAILED DESCRIPTION

While the specification concludes with claims particularly pointing out and distinctly claiming the invention, it is believed that the present invention will be better understood from the following description.

All percentages and ratios used hereinafter are by weight of total composition, unless otherwise indicated.

All measurements referred to herein are made at 25° C. unless otherwise specified.

All percentages, ratios, and levels of ingredients referred to herein are based on the actual amount of the ingredient, and do not include solvents, fillers, or other materials with which the ingredient may be combined as a commercially available product, unless otherwise indicated.

All publications, patent applications, and issued patents mentioned herein are hereby incorporated in their entirety by reference. Citation of any reference is not an admission regarding any determination as to its availability as prior art to the claimed invention.

Herein, "comprising" means that other steps and other components which do not affect the end result can be added. This term encompasses the terms "consisting of" and "consisting essentially of."

Organosiloxane Resins

Silicone resins are highly crosslinked polymeric siloxane systems. The crosslinking is introduced through the incorporation of tri-functional and tetrafunctional silanes with mono-functional or di-functional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of tri-functional and tetrafunctional siloxane monomer units, and hence, a sufficient level of crosslinking, such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0.

Silicone materials and silicone resins in particular can conveniently be identified according to a shorthand nomenclature system well known to those skilled in the art as the "MDTQ" nomenclature. Under this system, the silicone is described according to the presence of various siloxane monomer units which make up the silicone. Briefly, the symbol M denotes the mono-functional unit $(CH_3)_3SiO_{.5}$; D denotes the difunctional unit $(CH_3)_2SiO$; T denotes the trifunctional unit $(CH_3)SiO_{1.5}$; and Q denotes the quadra- or tetra-functional unit $SiO_2$. Note that a small amount, up to about 5% of silanol or alkoxy functionality may also be present in the resin structure as a result of processing.

Primes of the unit symbols, e.g., M', D', T', and Q', denote substituents other than methyl, and must be specifically defined for each occurrence. Typical alternate substituents include groups such as vinyl, phenyl, amino, hydroxyl, etc. The molar ratios of the various units, either in terms of subscripts to the symbols indicating the total number of each type of unit in the silicone, or an average thereof, or as specifically indicated ratios in combination with molecular weight, complete the description of the silicone material under the MDTQ system. Higher relative molar amounts of T, Q, T' and/or Q' to D, D', M and/or M' in a silicone resin is indicative of higher levels of crosslinking. As discussed before, however, the overall level of crosslinking can also be indicated by the oxygen to silicon ratio.

The organosiloxane resins are solid at about 25° C. and the average molecular weight of the resins is from about 1,000 to about 10,000. The resins are soluble in organic solvents such as toluene, xylene, isoparaffins, and cyclosiloxanes or the volatile carrier described below, indicating that the resin is not sufficiently crosslinked such that the resin is insoluble in the volatile carrier.

The silicone resins preferred for use herein are MQ, MT, MTQ, and MDTQ resins; such MQ resins are disclosed in U.S. Pat. No. 5,330,747, Krzysik, issued Jul. 19, 1994. Thus, the preferred silicone substituent is methyl. Especially preferred are MQ resins wherein the M:Q ratio is from about 0.5:1.0 to about 1.5:1.0. Organosiloxane resins such as these are commercially available, for example, Wacker 803 and 804 available from Wacker Silicones Corporation of Adrian, Mich., U.S., and G.E. 1170-002 (SR 1000) from the General Electric Company.

The level of the resin that is used in compositions is dependent on its degree of solubility in the formulation, particularly in the solvents used. Generally the range of resin used in the present invention is from about 5% to about 70%, preferably from about 15% to about 45% and most preferably from about 20% to about 40%.

Fluid Diorganopolysiloxane-based Polymers

In addition to the organosiloxane resins disclosed above, the compositions of the present invention may further comprise a fluid diorganopolysiloxane-based polymer to be combined with the organosiloxane resins. Said fluid diorganopolysiloxane-based polymers useful in the present invention span a large range of viscosities; from about 10 to about 10,000,000 centistokes (cSt) at 25° C. Some diorganopolysiloxane-based polymers useful in this invention exhibit viscosities greater than 10,000,000 centistokes (cSt) at 25° C. and therefore are characterized by manufacturer specific penetration testing. Examples of this characterization are GE silicone materials SE 30 and SE 63 with penetration specifications of 500–1500 and 250–600 (tenths of a millimeter) respectively.

Among the fluid diorganopolysiloxane polymers of the present invention are diorganopolysiloxane polymers comprising repeating units, where said units correspond to the formula $(R_2SiO)_n$, where R is a monovalent radical containing from 1 to 6 carbon atoms, preferably selected from the group consisting of methyl, ethyl, propyl, isopropyl, butyl, isobutyl, t-butyl, amyl, hexyl, vinyl, allyl, cyclohexyl, amino alkyl, phenyl, fluoroalkyl and mixtures thereof. The fluid diorganopoylsiloxane polymers employed in the present invention may contain one or more of these radicals as substituents on the siloxane polymer backbone. The fluid diorganopolysiloxane polymers may be terminated by triorganosilyl groups of the formula $(R'_3Si)$ where R' is a monovalent radical selected from the group consisting of radicals containing from 1–6 carbon atoms, hydroxyl groups, alkoxyl groups, and mixtures thereof. The fluid diorganopolysiloxane polymer must be compatible in solution with the organosiloxane resin and the volatile carrier. The term "compatible" refers to the formation of a single phase solution when the fluid diorganopolysiloxane polymer, the organosiloxane resin and the volatile carrier are mixed together in ratios required for a specific formulation. For example, the lower viscosity fluid diorganopolysiloxane polymers (viscosity of about 10 to 100 cSt.) are particularly useful when using ethanol as the principal volatile carrier. For higher viscosity polymers, e.g., poly(dimethylsiloxane), herein referred to as PDMS or silicone gum, having a viscosity of at least 100,000 cSt, volatile carriers other than ethanol are preferred.

Silicone gum corresponds to the formula:

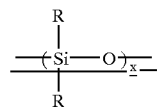

where R is a methyl group.

Fluid diorganopolysiloxane polymers such as these are commercially available, for example, SE 30 silicone gum and SF96 silicone fluid available from the General Electric Company. Similar materials can also be obtained from Dow Corning and from Wacker Silicones.

Another fluid diorganosiloxane-based polymer preferred for use in the present invention is a dimethicone copolyol to modify film forming characteristics as desired. The dimethicone copolyol can be further characterized as polyalkylene oxide modified polydimethysiloxanes, such as manufactured by the Witco Corporation under the trade name Silwet. Similar materials can be obtained from Dow Corning, Wacker Silicones and Goldschmidt Chemical Corporation as well as other silicone manufacturers.

In preferred embodiments of the present invention, the ratio of organosiloxane resin to fluid diorganopolysiloxane-based polymer is preferably from about 10:1 to about 1:10, preferably about 2:1 to about 8:1 and most preferably from about 4:1 to 6:1.

Volatile Carriers

In the present invention, the organosiloxane resin and the fluid diorganosiloxane-based polymer above must be easily transferred to the oral cavity surfaces, such as to the tooth enamel. To achieve delivery, it is necessary that the resin or the resin/polymer combination above be incorporated into a carrier, specifically a volatile carrier which must quickly volatilize from the oral cavity surfaces, leaving a film on the application surfaces. The volatile carrier must solubilize the organosiloxane resin and if present in the composition, the fluid diorganosiloxane polymer.

The volatile carrier comprises from about 10% to about 90%, preferably from about 15% to about 80%, and more preferably from about 20% to about 70% of the composition. The volatile carrier of the present invention is selected from the group consisting of hydrocarbon oils, volatile silicones, non-hydrocarbon solvents, and mixtures thereof.

Hydrocarbon oils useful in the present invention include those having boiling points in the range of 60–260° C., more preferably hydrocarbon oils having from about $C_8$ to about $C_{20}$ chain lengths, most preferably $C_8$ to $C_{20}$ isoparaffins. Of these isoparaffins most preferred are selected from the group consisting of isododecane, isohexadecane, isoeocosane, 2,2,4-trimethylpentane, 2,3-dimethylhexane and mixtures thereof. Most preferred is isododecane, available as, for example, Permethyl 99A from Permethyl Corporation corresponding to the formula:

Preferred volatile silicone fluids include cyclomethicones having 3, 4 and 5 membered ring structures corresponding to the formula:

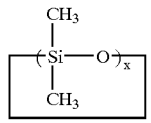

where X is from about 3 to about 6. Such volatile silicones include 244 Fluid, 344 Fluid and 245 Fluid, and 345 Fluid all from Dow Corning Corporation.

The general classes of non-hydrocarbon solvents useful herein include esters, ketones, alcohols, fluorocarbons and fluorocarbon ethers having boiling points in the range of 60 to 200° C. Non-hydrocarbon solvents or mixtures thereof particularly useful include those that are capable of solubilizing the resin and/or the diorganopolysiloxane-based polymer. Such solvents include but are not limited to ethanol, acetone, butanone, ethyl acetate, propyl acetate, amyl acetate, ethyl butyrate, methyl nonafluoroisobutyl ether, methyl nonafluorobutyl ether, and mixtures thereof. These non-hydrocarbon solvents are readily available such as ethyl acetate and methyl ethyl ketone, both supplied by J. T. Baker of Phillispburg, N.J., and HFE (a mixture of methyl nonafluoroisobutyl ether and methyl nonafluorobutyl ether), supplied by the 3M Company.

Rheology Modifiers

The compositions further comprise a rheology modifier which inhibits settling and separation of components or controls settling in a manner which facilitates re-dispersion and may control rheological flow properties. Suitable rheology modifiers herein include organo modified clays, silicas, polyethylene, and mixtures thereof. The preferred organophilic clays comprise quatemium-18 hectorite or Stearalkonium hectorite, such as Bentone 27 and 38™ from Rheox, organoclay dispersion such as Bentone ISD gel™; or bentonite organo modified clays such as Bentone 34™ from Rheox or the Claytone Series™ from Southern Clay Products; and mixtures thereof. The preferred silicas may be fumed silica such as the Aerosil™ series from Degussa or the Cab-o-sil™ series from Cabot Corporation, silica gels such as the Sylodent™ or Sylox™ series from W. R. Grace & Co. or precipitated silica such as Zeothix 265 from J. M. Huber Corporation.

The rheology modifier is preferably present in the composition at a level of from about 0.1% to about 30%, preferably from about 0.5% to about 10%, and even more preferably 1% to about 3% of the composition.

Oral Care Substances

The oral care substance preferably contains an active at a level where upon directed use, the benefit sought by the wearer is promoted without detriment to the oral surface to which it is applied. Examples of the oral conditions these actives address include, but, are not limited to, appearance and structural changes to teeth, whitening, stain bleaching, stain removal, plaque removal, tartar removal, cavity prevention and treatment, inflamed and/or bleeding gums, mucosal wounds, lesions, ulcers, aphthous ulcers, cold sores, tooth abscesses, and the elimination of mouth malodor resulting from the conditions above and other causes such as microbial proliferation.

Suitable oral care substances include any material that is generally considered safe for use in the oral cavity and that provides changes to the overall appearance and/or health of the oral cavity. The level of oral care substance in the compositions of the present invention is generally, unless specifically noted, from about 0.01% to about 50%, preferably from about 0.1% to about 20%, more preferably from about 0.5% to about 10%, and even more preferably from about 1% to about 7%, by weight of the composition.

Oral care compositions or substances of the present invention may include many of the actives previously disclosed in the art. The following is a non-limiting list of oral care actives that may be used in the present invention.

1. Teeth Color Modifying Substances

Teeth color modifying substances may be considered among the oral care substance useful in the present invention. These substances are suitable for modifying the color of the teeth to satisfy the consumer. These substances comprise particles that when applied on the tooth surface modify that surface in terms of absorption and, or reflection of light. Such particles provide an appearance benefit when a film containing such particles is applied over the surfaces of a tooth or teeth. This benefit may last to the point wherein the film has eroded, presenting for example a mottled or non-uniform looking tooth surface.

Particles most useful in the present invention include pigments and colorants routinely used in the cosmetic arts. There are no specific limitations as to the pigment and, or colorant used in the present composition other than the limitation of the effect it has on the light source upon the teeth surfaces. Pigments and colorants include inorganic white pigments, inorganic colored pigments, pearling agents, filler powders and the like; see Japanese Published Patent Application Kokai No. 9 [1997]-100215, published Apr. 15, 1997, incorporated herein by reference. Specific examples are selected from the group consisting of talc, mica, magnesium carbonate, calcium carbonate, magnesium silicate, aluminum magnesium silicate, silica, titanium dioxide, zinc oxide, red iron oxide, brown iron oxide, yellow iron oxide, black iron oxide, ferric ammonium ferrocyanide, manganese violet, ultramarine, nylon powder, polyethylene powder, methacrylate powder, polystyrene powder, silk powder, crystalline cellulose, starch, titanated mica, iron oxide titanated mica, bismuth oxychloride, and mixtures thereof. Most preferred are those selected from the group consisting of titianium dioxide, bismuth oxychloride, zinc oxide and mixtures thereof. Pigments that are generally recognized as safe, and are listed in C.T.F.A. Cosmetic Ingredient Handbook, 3rd Ed., Cosmetic and Fragrance Assn., Inc., Washington D.C. (1982), incorporated herein by reference.

The pigments are typically used as opacifiers and colorants. These pigments can be used as treated particles, or as the raw pigments themselves. Typical pigment levels are selected for the particular impact that is desirable by the consumer. For example, teeth that are particularly dark or stained one would typically use pigments in sufficient amount to lighten the teeth. On the other hand, where individual teeth or spots on the teeth are lighter than other teeth, pigments to darken the teeth may be useful. The levels of pigments and colorants are generally used in the range of about 0.05% to about 20%, preferably from about 0.10% to about 15% and most preferably from about 0.25% to about 10% of the composition.

In place of or in addition to pigments and colorants, teeth modifying substances include materials that remove or bleach intrinsic or extrinsic stains on or in the tooth surfaces. Such substances are selected from the group consisting of the peroxides, metal chlorites, perborates, percarbonates, peroxyacids, persulfates, and combinations thereof. Suitable peroxide compounds include hydrogen peroxide, urea peroxide, calcium peroxide, carbamide peroxide, and mixtures thereof. Most preferred is carbamide peroxide. Suitable metal chlorites include calcium chlorite, barium chlorite, magnesium chlorite, lithium chlorite, sodium chlorite, and potassium chlorite. Additional bleaching substances may be hypochlorite and chlorine dioxide. The preferred chlorite is sodium chlorite. A preferred percarbonate is sodium percarbonate. Preferred persulfates are oxones. The level of these substances is dependent on the available oxygen or chlorine respectively that the molecule is capable of providing to bleach the stain. This level is generally used in compositions of the present invention at levels from about 0.1% to about 35%, preferably from about 1% to about 25% and most preferably from about 5% to about 10% of the composition.

2. Anti-tartar Agents

Anti-tartar agents known for use in dental care products include phosphates. Phosphates include pyrophosphates, polyphosphates, polyphosphonates and mixtures thereof. Pyrophosphates are among the best known for use in dental care products. Pyrophosphate and polyphosphate ions are delivered to the teeth derive from pyrophosphate polyphosphate salts. The pyrophosphate salts useful in the present compositions include the dialkali metal pyrophosphate salts, tetra-alkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms are the preferred species. While any of the above mentioned pyrophosphate salts may be used, tetrasodium pyrophosphate salt is preferred. Sodium polyphosphate and triethanolamine polyphosphates, for example, are preferred.

The pyrophosphate salts are described in more detail in Kirk & Othmer, *Encyclopedia of Chemical Technology*, Third Edition, Volume 17, Wiley-lnterscience Publishers (1982). Additional anticalculus agents include pyrophosphates or polyphosphates disclosed in U.S. Pat. No. 4,590,066 issued to Parran & Sakkab on May 20, 1986; polyacrylates and other polycarboxylates such as those disclosed in U.S. Pat. No. 3,429,963 issued to Shedlovsky on Feb. 25, 1969 and U.S. Pat. No. 4,304,766 issued to Chang on Dec. 8, 1981; and U.S. Pat. No. 4,661,341 issued to Benedict & Sunberg on Apr. 28, 1987; polyepoxysuccinates such as those disclosed in U.S. Pat. No. 4,846,650 issued to Benedict, Bush & Sunberg on Jul. 11, 1989; ethylenediaminetetraacetic acid as disclosed in British Patent No. 490,384 dated Feb. 15, 1937; nitrilotriacetic acid and related compounds as disclosed in U.S. Pat. No. 3,678,154 issued to Widder & Briner on Jul. 18, 1972; polyphosphonates as disclosed in U.S. Pat. No. 3,737,533 issued to Francis on Jun. 5, 1973, U.S. Pat. No. 3,988,443 issued to Ploger, Schmidt-Dunker & Gloxhuber on Oct. 26, 1976 and U.S. Pat. No. 4,877,603 issued to Degenhardt & Kozikowski on Oct. 31, 1989. Anticalculus phosphates include potassium and sodium pyrophosphates; sodium tripolyphosphate; diphosphonates, such as ethane-1-hydroxy-1,1-diphosphonate, 1-azacycloheptane-1,1-diphosphonate, and linear alkyl diphosphonates; linear carboxylic acids; and sodium zinc citrate.

Agents that may be used in place of or in combination with the pyrophosphate salt include such known materials as synthetic anionic polymers including polyacrylates and copolymers of maleic anhydride or acid and methyl vinyl ether (e.g., Gantrez), as described, for example, in U.S. Pat. No. 4,627,977, to Gaffar et al.; as well as, e.g., polyamino propoane sulfonic acid (AMPS), zinc citrate trihydrate, polyphosphates (e.g., tripolyphosphate; hexametaphosphate), diphosphonates (e.g., EHDP; AHP), polypeptides (such as polyaspartic and polyglutamic acids), and mixtures thereof.

3. Fluoride Ion Source

Fluoride ion sources are well known for use in oral care compositions as anticaries agents. Fluoride ions are contained in a number of oral care compositions for this purpose, particularly toothpastes. Patents disclosing such toothpastes include U.S. Pat. No. 3,538,230, Nov. 3, 1970 to Pader et al; U.S. Pat. No. 3,689,637, Sep. 5, 1972 to Pader; U.S. Pat. No. 3,711,604, Jan. 16, 1973 to Colodney et al; U.S. Pat. No. 3,911,104, Oct. 7, 1975 to Harrison; U.S. Pat. No. 3,935,306, Jan. 27, 1976 to Roberts et al; and U.S. Pat. No. 4,040,858, Aug. 9, 1977 to Wason.

Application of fluoride ions to dental enamel serves to protect teeth against decay. A wide variety of fluoride ion-yielding materials can be employed as sources of soluble fluoride in the instant compositions. Examples of suitable fluoride ion-yielding materials are found in Briner et al; U.S. Pat. No. 3,535,421; issued Oct. 20, 1970 and Widder et al; U.S. Pat. No. 3,678,154; issued Jul. 18, 1972. Preferred fluoride ion sources for use herein include sodium fluoride, potassium fluoride and ammonium fluoride. Sodium fluoride is particularly preferred. Preferably the instant compositions provide from about 50 ppm to 10,000 ppm, more preferably from about 100 to 3000 ppm, of fluoride ions in the compositions that contact dental surfaces when used with the delivery system of the present invention.

4. Anti-microbial Agents

Anti-microbial agents can also be present in the oral care compositions or substances of the present invention. Such agents may include, but are not limited to, 5-chloro-2-(2,4-dichlorophenoxy)-phenol, commonly referred to as triclosan, and described in *The Merck Index*, 11th ed. (1989), pp. 1529 (entry no. 9573) in U.S. Pat. No. 3,506,720, and in European Patent Application No. 0,251,591 of Beecham Group, PLC, published Jan. 7, 1988; phthalic acid and its salts including, but not limited to those disclosed in U.S. Pat. No. 4,994,262, Feb. 19, 1991, preferably magnesium monopotassium phthalate, chlorhexidine (*Merck Index*, no. 2090), alexidine (*Merck Index*, no. 222; hexetidine (*Merck Index*, no. 4624); sanguinarine (*Merck Index*, no. 8320); benzalkonium chloride (*Merck Index*, no. 1066); salicylanilide (*Merck Index*, no. 8299); domiphen bromide (*Merck Index*, no. 3411); cetylpyridinium chloride (CPC) (*Merck Index*, no. 2024; tetradecylpyridinium chloride (TPC); N-tetradecyl-4-ethylpyridinium chloride (TDEPC); octenidine; delmopinol, octapinol, and other piperidino derivatives; nicin preparations; zinc/stannous ion agents; antibiotics such as augmentin, amoxicillin, tetracycline, doxycycline, minocycline, and metronidazole; and analogs and salts of the above; essential oils including thymol, geraniol, carvacrol, citral, hinokitiol, eucalyptol, catechol (particularly 4-allyl catechol) and mixtures thereof; methyl salicylate; hydrogen peroxide; metal salts of chlorite and mixtures of all of the above.

5. Anti-inflammatory Agents

Anti-inflammatory agents can also be present in the oral care compositions or substances of the present invention. Such agents may include, but are not limited to, non-steroidal anti-inflammatory agents or NSAIDs such as ketorolac, flurbiprofen, ibuprofen, naproxen, indomethacin, aspirin, ketoprofen, piroxicam and meclofenamic acid. Use of NSAIDs such as Ketorolac are claimed in U.S. Pat. No. 5,626,838, issued May 6, 1997. Disclosed therein are methods of preventing and, or treating primary and reoccurring squamous cell carcinoma of the oral cavity or oropharynx by topical administration to the oral cavity or oropharynx an effective amount of an NSAID.

6. Nutrients

Nutrients may improve the condition of the oral cavity and can be included in the oral care compositions or substances of the present invention. Nutrients include minerals, vitamins, oral nutritional supplements, enteral nutritional supplements, and mixtures thereof.

Minerals that can be included with the compositions of the present invention include calcium, phosphorus, fluoride, zinc, manganese, potassium and mixtures thereof. These minerals are disclosed in Drug Facts and Comparisons (loose leaf drug information service), Wolters Kluer Company, St. Louis, Mo., ©1997, pp10–17.

Vitamins can be included with minerals or used separately. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Such vitamins are disclosed in *Drug Facts and Comparisons* (loose leaf drug information service), Wolters Kluer Company, St. Louis, Mo., ©1997, pp. 3–10.

Oral nutritional supplements include amino acids, lipotropics, fish oil, and mixtures thereof, as disclosed in *Drug Facts and Comparisons* (loose leaf drug information service), Wolters Kluer Company, St. Louis, Mo., ©1997, pp. 54–54e. Amino acids include, but, are not limited to L-Tryptophan, L-Lysine, Methionine, Threonine, Levocarnitine or L- carnitine and mixtures thereof. Lipotropics include, but, are not limited to choline, inositol, betaine, linoleic acid, linolenic acid, and mixtures thereof. Fish oil contains large amounts of Omega-3 (N-3) Polyunsaturated fatty acids, eicosapentaenoic acid and docosahexaenoic acid.

Enteral nutritional supplements include, but, are not limited to protein products, glucose polymers, corn oil, safflower oil, medium chain triglycenides as disclosed in *Drug Facts and Comparisons* (loose leaf drug information service), Wolters Kluer Company, St. Louis, Mo., ©1997, pp. 55–57.

7. Mouth and Throat Products

Other materials that can be used with the present invention include commonly known mouth and throat products. Such products are disclosed in *Drug Facts and Comparisons* (loose leaf drug information service), Wolters Kluer Company, St. Louis, Mo., ©1997, pp. 520b–527. These products include, but, is are not limited to anti-fungal, antibiotic and analgesic agents.

8. Antioxidants

Antioxidants are generally recognized as useful in compositions such as those of the present invention. Antioxidants are disclosed in texts such as Cadenas and Packer, *The Handbook of Antioxidants*, ©1996 by Marcel Dekker. Inc. Antioxidants that may be included in the oral care composition or substance of the present invention include, but are not limited to Vitamin E, ascorbic acid, Uric acid, carotenoids, Vitamin A, flavonoids and polyphenols, herbal antioxidants, melatonin, aminoindoles, lipoic acids and mixtures thereof.

9. H-2 Antagonists

Histamine-2 (H-2 or H2) receptor antagonist compounds (H-2 antagonists) may be used in the oral care composition of the present invention. As used herein, selective H-2 antagonists are compounds that block H-2 receptors, but do not have meaningful activity in blocking histamine-1 (H-1 or H1) receptors. Selective H-2 antagonists stimulates the contraction of smooth muscle from various organs, such as the gut and bronchi; this effect can be suppressed by low concentrations of mepyramine—a typical antihistaminic drug. The pharmacological receptors involved in these mepyramine-sensitive histamine responses have been defined as H-1 receptors (Ash, A. S. F. & H. O. Schild, Brit. J. Pharmacol Chemother., Vol. 27 (1966), p. 427. Histamine also stimulates the secretion of acid by the stomach (Loew, E. R. & O. Chickering, Proc. Soc. Exp. Biol. Med., Vol. 48 (1941), p. 65), increases the heart rate (Trendelenburg, U., J. Pharmacol., Vol. 130 (1960), p. 450), and inhibits contractions in the rat uterus (Dews, P. B. & J. D. P. Graham, Brit. J. Pharmacol. Chemother., Vol. 1 (1946), p. 278); these actions cannot be antagonized by mepyramine and related drugs. The H-2 antagonists useful in the oral care compositions or substances are those that blockade the receptors involved in mepyramine-insensitive, non-H-1 (H-2), histamine responses, and do not blockade the receptors involved in mepyramine-sensitive histamine responses.

Selective H-2 antagonists are those compounds found to be H-2 antagonists through their performance in classical preclinical screening tests for H-2 antagonist function. Selective H-2 antagonists are identified as compounds which can be demonstrated to function as competitive or non-competitive inhibitors of histamine-mediated effects in those screening models specifically dependent upon H-2 receptor function, but to lack significant histamine antagonist activity in those screening models dependent upon H-1 receptor function. Specifically, this includes compounds that would be classified as described by Black, J. W., W. A. M. Duncan, C. J. Durant, C. R. Ganellin & E. M. Parsons, "Definition and Antagonism of Histamine H2-Receptors", Nature, Vol. 236 (Apr. 21, 1972), pp. 385–390 (Black), as H-2 antagonists if assessed as described by Black through testing with the guinea pig spontaneously beating right atria in vitro assay and the rat gastric acid secretion in vivo assay, but shown to lack in significant H-1 antagonist activity relative to H-2 antagonist activity, if assessed as described by Black with either the guinea pig ileum contraction in vitro assay or the rat stomach muscle contraction in vivo assay. Preferably selective H-2 antagonists. demonstrate no significant H-1 activity at reasonable dosage levels in the above H-1 assays. Typical reasonable dosage level is the lowest dosage level at which 90% inhibition of histamine, preferably 99% inhibition of histamine, is achieved in the above H-2 assays.

Selective H-2 antagonists include compounds meeting the above criteria which are disclosed in U.S. Pat. Nos. 5,294,433 and 5,364,616 Singer et al., issued Mar. 15, 1994 and Nov. 15, 1994 respectively and assigned to Procter & Gamble, wherein the selective H-2 antagonist is selected from the group consisting of cimetidine, etintidine, ranitidine, ICIA-5165, tiotidine, ORF-17578, lupitidine, donetidine, famotidine, roxatidine, pifatidine, lamtidine, BL-6548, BMY-25271, zaltidine, nizatidine, mifentidine, BMY-25368 (SKF-94482), BL-6341A, ICI-162846, ramixotidine, Wy-45727, SR-58042, BMY-25405, loxtidine, DA-4634, bisfentidine, sufotidine, ebrotidine, HE-30–256, D-16637, FRG-8813, FRG-8701, impromidine, L-643728, and HBA08. Particularly preferred is cimetidine (SKF-92334), N-cyano-N'-methyl-N"-(2-(((5-methyl-1H-imidazol-4-yl)methyl)thio)ethyl)guanidine:

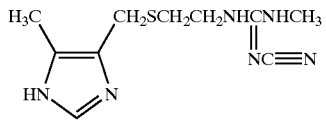

Cimetidine is also disclosed in the Merck Index, 11th edition (1989), p. 354 (entry no. 2279), and Physicians' Desk Reference, 46th edition (1992), p. 2228. Related preferred H-2 antagonists include burimamide and metiamide.

10. Analgesic Actives

Anti-pain or desensitizing agents can also be present in the oral care compositions or substances of the present invention. Such agents may include, but are not limited to, strontium chloride, potassium nitrate, natural herbs such as gall nut, Asarum, Cubebin, Galanga, scutellaria, Liangmianzhen, Baizhi, etc.

11. Anti-Viral Actives

Antiviral actives useful in the present composition include any know actives that are routinely use to treat viral infections. Such anti-viral actives are disclosed in Drug Facts and Comparisons (loose leaf drug information service), Wolters Kluer Company, St. Louis, Mo., ©1997, pp. 402(a)–407(z), incorporated herein by reference in its entirety. Specific examples include anti-viral actives disclosed in U.S. Pat. No. 5,747,070, issued May 5, 1998 to Satyanarayana Majeti, incorporated herein by reference in its entirety. Said Patent discloses the use of stannous salts to control viruses. Stannous salts and other anti-viral actives are described in detail in Kirk & Othmer, Encyclopedia of Chemical Technology, Third Edition, Volume 23, Wiley-lnterscience Publishers (1982), pp. 42–71, incorporated herein by reference in its entirety. The stannous salts that may be used in the present invention would include organic stannous carboxylates and inorganic stannous halides. While stannous fluoride may be used, it is typically used only in combination with another stannous halide or one or more stannous carboxylates or another therapeutic agent.

12. Other Ingredients

In addition to the above materials of the composition of the present invention, a number of other components may desirably be added to the oral care substance. Additional components include, but are not limited to, flavoring agents, sweetening agents, xylitol, surfactants, and chelants such as ethylenediaminetetraacetic acid. Suitable flavoring agents include, but are not limited to, oil of peppermint, oil of sassafras, clove bud oil, peppermint, menthol, anethole, thymol, methyl salicylate, eucalyptol, cassia, 1-menthyl acetate, sage, eugenol, parsley oil, oxanone, oil of wintergreen, alpha-irisone, oil of spearmint, marjoram, lemon, orange, propenyl guaethol, cinnamon, and mixtures thereof.

These additional ingredients can also be used in place of the compounds disclosed above.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

TABLE 1

Hydrophobic Oral Care Composition

| Component | Ex. 1 | Ex. 2 | Ex. 3 | Ex. 4 | Ex. 5 | Ex. 6 |
|---|---|---|---|---|---|---|
| Organosiloxane Resin[1] | 25 | 25 | 24.6 | 25 | 25 | 25 |
| Silicone Gum[2] | 12.5 | 4.2 | 3.5 | 2.5 | 1.8 | — |
| Oral Care Substance | 17 | 17 | 17 | 17 | 17 | 17 |
| Volatile Carrier[3] | 144.5 | 52.8 | 53.9 | 54.5 | 55.2 | 57.0 |
| Bentone Clay[4] | 1 | 1 | 1 | 1 | 1 | 1 |
| TOTAL | 100 | 100 | 100 | 100 | 100 | 100 |

[1]. E.g., MQ resin available as 1170-002 from General Electric.
[2]. E.g., Dimethicone gum available as SE 63 or SE 30 from General Electric.
[3]. E.g., Isododecane or a 50/50 mixture of ethyl acetate and butanone or a mixture of ethyl acetate, propyl acetate and HFE. The percentage of each individual solvent component in the mixed solvent systems can vary from 0 to 100%, respectively.
[4]. Bentone 27 available from Rheox.

Method of Preparation

The compositions of Table 1 are non-aqueous. The oral care substances are dispersed or dissolved in a solution comprising the organosiloxane resin, the fluid diorganopolysiloxane polymer, the volatile carrier, and the rheology modifier.

The hydrophobic compositions of Table 1 are suitably prepared as follows. Three hundred (300) grams of organosiloxane resin solution (for example, 43.7% MQ resin solution in isododecane or in a 50/50 mixture of ethyl acetate and butanone or in a mixture of ethyl acetate, propyl acetate and HFE) are mixed with 147.30 grams of fluid diorganopolysiloxane polymer solution (for example, 50% SE 30 silicone gum solution in isododecane or a 50/50 mixture of ethyl acetate and butanone or a mixture of ethyl acetate, propyl acetate and HFE). The oral care substances are then dispersed in the resin/gum mixture. This method may be carried out without the presence of the silicone gum.

All oral care substances described herein can formulated as described above. The compositions described in the following Table 1a may be prepared using the above method.

TABLE 1a

Hydrophobic Oral Care Compositions

| Component | Ex. 1 | Ex. 2 | Ex. 3 | Ex. 4 |
|---|---|---|---|---|
| Organosiloxane Resin[1] | 33.43 | 33.43 | 35.14 | 33.43 |
| Silicone Gum[2] | 5.57 | 5.57 | 5.86 | 5.57 |
| Oral Care Substance | 19.00 | 12.00 | 19.00 | 19.00 |
| Ethyl acetate | 8.00 | 8.50 | 8.00 | 8.00 |
| Bentone Gel[3] | 10.00 | 10.00 | 10.00 | 10.00 |
| DC-200/350cst.[4] | 1.00 | 1.00 | 2.00 | 1.00 |
| HFE-7100[5] | 21.00 | 26.00 | — | 19.50 |
| N-propyl acetate | 2.00 | 2.00 | — | 2.00 |
| 2-butanone | — | — | 19.00 | — |
| Aerosil 200[6] (SiO$_2$) | — | — | 1.00 | — |
| Flavor | — | 1.50 | — | 1.50 |
|  | 100.00 | 100.00 | 100.00 | 100.00 |

[1]. E.g., MQ resin available as 1170-002 from General Electric.
[2]. E.g., Dimethicone gum available as SE 30 from General Electric.
[3]. Bentone Gel IPM available from Rheox.
[4]. DC-200/350 is: dimethylpolysiloxane, CAS# 9016-00-6, from Dow Corning.
[5]. HFE-7100 is a mixture of Methyl Nonafluoroisobutyl Ether, CAS# 163702-08-7 and Methyl Nonafluorobutyl Ether, CAS# 163702-07-6 manufactured by 3M Co.
[6]. Aerosil 200 is silicon dioxide (chemically prepared), CAS# 112945-52-5, from Degussa AG.

TABLE 2a

Teeth Color Modifying Compositions

| Component | Ex. 1 | Ex. 2 | Ex. 3 | Ex. 4 | Ex. 5 | Ex. 6 |
|---|---|---|---|---|---|---|
| Ethyl Acetate | 26.00 | 22.00 | 34.00 | 28.00 | 25.77 | 23.00 |
| 2-Butanone | 25.95 | 17.00 | 9.00 | 14.50 | 25.50 | 23.45 |
| Isododecane | — | 10.00 | — | — | 5.00 | — |
| Limonene | — | 4.00 | — | — | — | — |
| MQ Resin | 28.00 | 32.50 | 33.00 | 35.00 | 27.00 | 28.00 |
| SE 30 Silicone Gum | 7.00 | — | 11.00 | 5.00 | 3.00 | 7.00 |
| Silicone Fluid (10cStk) | — | 6.50 | — | — | — | — |
| Bentone Gel ISD | 10.00 | — | 8.00 | 10.00 | 10.00 | — |
| Claytone HY | — | 2.00 | — | — | — | 7.00 |
| Cab-o-Sil | — | — | 1.50 | — | — | — |
| Bismuth Oxychloride | — | 5.00 | — | — | — | 10.00 |
| Titanium Dioxide | 3.0 | — | 1.00 | 5.00 | 2.00 | — |
| Flavor Oil | — | 0.10 | — | 0.15 | 0.15 | — |
| Polymethyl-silsesquioxane | — | — | 1.00 | — | — | — |
| Polymethyl-methacrylate | — | 1.00 | — | — | 0.50 | — |
| Nylon 12 | — | — | — | 2.00 | — | 1.00 |
| Silica | — | — | — | — | 0.50 | — |
| F&D&C Yellow #5 Aluminum Lake | 0.05 | — | 0.10 | — | 0.05 | 0.10 |
| Iron Oxide, red | — | — | — | 0.50 | 0.03 | — |
| Sodium Fluoride | — | — | 1.0 | — | — | — |
| Sodium Saccharin | — | — | 0.30 | — | 0.50 | 0.30 |
|  | 100.00 | 100.00 | 100.00 | 100.00 | 100.00 | 100.00 |

TABLE 2b

Teeth Color Modifying Compositions

| Component | Ex. 7 | Ex. 8 | Ex. 9 | Ex. 10 | Ex. 11 | Ex. 12 |
|---|---|---|---|---|---|---|
| Ethyl Acetate | 18.00 | 14.85 | 22.25 | 20.88 | 18.96 | 18.00 |
| 2-Butanone | 18.00 | 13.00 | 13.10 | 20.88 | 10.00 | 18.00 |
| Isododecane | — | 10.00 | — | — | 11.54 | — |
| Limonene | — | 4.35 | — | — | 5.00 | — |
| MQ Resin | 28.00 | 32.50 | 26.50 | 27.33 | 36.00 | 31.50 |
| SE 30 Silicone Gum | 7.00 | — | 8.80 | 13.67 | — | — |
| Silicone Visc-100 M | — | — | — | — | — | 3.50 |
| Silicone Fluid (10cStk) | — | 6.50 | — | — | 9.00 | — |
| Bentone Gel ISD | 10.00 | — | 6.40 | 9.95 | — | 10.00 |
| Claytone HY | — | 2.45 | — | — | 3.00 | — |
| Cab-o-Sil | — | — | 1.50 | — | — | — |
| Sodium Percarbonate | 19.00 | — | 19.00 | 7.00 | — | 19.00 |
| Carbamide Peroxide | — | 15.00 | — | — | 5.00 | — |
| Bismuth Oxychloride | — | 1.15 | — | — | — | — |
| Titanium Dioxide | — | — | 1.00 | — | 1.50 | — |
| Flavor Oil | — | — | 0.15 | — | — | — |
| Sodium Fluoride | — | — | 1.00 | — | — | — |
| Sodium Saccharin | — | 0.20 | 0.30 | 0.30 | — | — |

TABLE 2c

Ethanol Based Teeth Color Modifying Compositions

| Component | Ex. 1 | Ex. 2 | Ex. 3 | Ex. 4 | Ex. 5 | Ex. 6 |
|---|---|---|---|---|---|---|
| Ethanol | 25.71 | 23.10 | 41.70 | 39.60 | 23.55 | 23.50 |
| Ethyl Acetate | — | 4.25 | — | — | — | — |
| Ethyl Butyrate | 12.74 | 11.75 | — | 6.30 | 10.90 | 11.40 |
| Isoamyl Acetate | — | — | — | — | 2.65 | — |
| Isododecane | — | — | — | 8.00 | — | — |
| MQ Resin | 47.00 | 42.00 | 41.75 | 36.33 | 41.80 | 39.00 |
| Silicone Visc-100 M | — | 7.10 | — | — | — | — |
| Silicone Fluid 100cSt | 9.65 | — | — | — | 8.55 | 8.55 |
| Silicone Fluid 10cStk | — | 4.00 | 11.05 | — | — | 4.30 |
| Silwet L-7500 | — | — | — | — | 6.85 | — |
| Bentone 27 | 1.85 | 1.35 | 2.00 | 2.27 | 1.97 | 1.70 |
| Cab-o-Sil | — | 0.45 | — | — | — | — |
| Bismuth Oxychloride | — | 5.00 | — | — | — | 10.00 |
| Titanium Dioxide | 3.00 | — | 1.00 | 5.00 | 2.00 | — |
| Flavor Oil | — | 0.10 | — | 0.15 | 0.15 | — |
| Polymethyl-silsesquioxane | — | — | 1.00 | — | — | — |
| Polymethyl-methacrylate | — | 1.00 | — | — | 0.50 | — |
| Nylon 12 | — | — | — | 2.00 | — | 1.00 |
| silica | — | — | — | — | 0.50 | — |
| FD&C Yellow #5 Al Lake | 0.05 | — | 0.10 | — | 0.05 | 0.10 |
| Iron Oxide, Red | — | — | — | 0.50 | 0.03 | — |
| Sodium Fluoride | — | — | 1.00 | — | — | — |
| Sodium Saccharin | — | — | 0.30 | — | 0.50 | 0.30 |
|  | 100.00 | 100.00 | 100.00 | 100.00 | 100.00 | 100.00 |

TABLE 3

Oral Care Compositions

| Component | Ex. 1 | Ex. 2 | Ex. 3 | Ex. 4 | Ex. 5 |
|---|---|---|---|---|---|
| Ethyl Acetate | 24.50 | 27.75 | 22.00 | 19.96 | 21.10 |
| 2-Butanone | 24.50 | 16.30 | 22.00 | 10.00 | 21.10 |
| Isododecane | — | — | — | 11.54 | — |
| Limonene | — | — | — | 5.00 | — |
| MQ Resin | 30.40 | 33.00 | 28.80 | 36.00 | 32.84 |
| SE 30 Silicone Gum | 7.60 | 11.00 | 14.40 | — | 8.21 |
| Silicone Fluid 10cStk | — | — | — | 9.00 | — |
| Bentone Gel ISD | 10.00 | 8.00 | 10.50 | — | 11.75 |
| Claytone HY | — | — | — | 3.00 | — |
| Cab-o-Sil | — | 1.50 | — | — | — |
| Bismuth Oxychloride | — | 1.00 | — | — | — |
| Titanium Dioxide | — | — | — | 2.00 | — |
| Flavor Oil | — | 0.15 | — | — | — |
| Potassium Nitrate | — | — | — | — | 5.00 |
| Sodium Chlorite | 3.00 | — | — | — | — |
| Tripoilphosphate | — | — | — | 2.50 | — |
| Sodium Fluoride | — | 1.00 | — | 1.00 | — |
| Chlorhexidine Gluconate | — | — | 2.00 | — | — |
| Sodium Saccharin | — | 0.30 | 0.30 | — | — |
| | 100.00 | 100.00 | 100.00 | 100.00 | 100.00 |

Method of Preparation

The compositions of Tables 2a, 2b, 2c and 3 are suitably prepared as followed. Add approximately 90% of the solvents into a container suitable to minimize solvent loss. Add approximately 75% of rheology modifiers and mix until well dispersed. Add about 90% of the silicone resin and mix until completely dissolved. Add the silicone gum and, or silicone fluids and mix until completely dissolved. Alternatively premixes of the silicone resin and/or the silicone gum may be prepared prior to incorporation into the final blending step to facilitate silicone dissolution and ease of manufacturing. Depending on the formula composition, the order of ingredient addition may also vary such as the addition of the rheology modifier(s) may be moved to a later step allowing lower viscosity to be maintained until the later stages of the blending step. At this time add any salts such as sodium percarbonate and other oral care actives, aesthetic ingredients such as sweeteners, dyes, and flavors. Continue mixing until homogeneous. Additional high shear mixing may be used to promote the mixing.

In a separate vessel add the remainder of the silicone resin, rheology modifiers, the pigments and approximately 10% of the solvent. Mix until it is a homogeneous slurry. Add this slurry to the mixture above after running the slurry through an ultrasonic processor such as a Vibra-Cell Ultrasonic Processor, available from Sonics & Materials, Inc., Newtown, Conn. Mix the composition until homogeneous and pack into air tight containers.

The embodiments disclosed and represented by the examples of the previous Tables have many advantages. For example, they provide better durability and subsequent delivery of oral care substances, particularly to the surfaces of the teeth. They also provide a convenient, discrete, and easy to use product form which can deliver benefits that are significantly different from those that can be achieved by conventional product forms.

Method of Use

In practicing the present invention, the user need only apply a composition herein that contains the oral care substance or substances necessary in order to obtain a desired effect, e.g. teeth color modification, breath freshening, caries prevention, pain relief, gum health, tartar control, etc. to the tooth surfaces in the areas desired. The compositions may also be applied to other surfaces of the oral cavity, such as the gingival or mucosal tissues, or to any other oral cavity surface. The composition can be applied with a brush, a pen applicator, a doe's foot applicator, or the like, or even with the fingers.

A film containing the oral care substance quickly forms on the surface to which the composition has been applied. Prolonged delivery of the oral care substance is made possible as the oral care substance is released from the film over time. Then, any residual oral care substance may be easily removed by wiping, brushing or rinsing the oral surface after a desired period of time has elapsed, or in the normal course of tooth brushing or other oral care activities. Without being bound by theory, it is believed that the film will last from about 2 hours to 8 hours regardless of the reactivity of the oral care substance. Preferably, the compositions are almost unnoticeable when applied to the oral cavity.

It is not necessary to prepare the oral cavity before applying the composition of the present invention. For example, the user may or may not choose to brush the teeth or rinse the mouth before applying the composition. The surfaces of the oral cavity are neither required to be dried nor to be excessively wet with saliva or water before the composition is applied. However, it is believed that adhesion to the tooth enamel surfaces will be improved if the teeth are dry when the composition is applied.

It should be understood that the present invention relates not only to methods for delivering an oral care substance to the oral cavity of a human, but also to methods of delivering an oral care substance to the oral cavity of an animal, e.g., household pets or other domestic animals, or animals kept in captivity.

It is understood that the examples and embodiments described herein are for illustrative purposes only and that various modifications or changes in light thereof will be suggested to one skilled in the art without departing from the scope of the present invention.

What is claimed is:

1. A composition for delivering an oral care substance to the oral cavity, comprising:
   (a) an organosiloxane resin;
   b) a volatile carrier capable of solubilizing the organosiloxane resin;
   (c) a rheology modifying agent; and
   (d) at least one oral care substance comprising particles suitable for modifying the color of the teeth and providing an appearance benefit to the teeth when the composition containing such puticles is applied to the tee surfaces, wherein the particles are pigments selected from the group consisting of talc, mica, magnesium carbonate, calcium carbonate, magnesium silicate, aluminum magnesium silicate, silica, titanium dioxide, zinc oxide, red iron oxide, yellow iron oxide, black iron oxide, ultramarinc, nylon powder, polyethylene powder, methacrylate powder, polystyrene powder, silk powder, crystalline cellulose, stach, titanated mica, iron oxide titanated mica, bismuth oxychloride, and mixtures thereof.

2. The composition of claim 1 wherein the organosiloxane resin is selected from the group consisting of $(CH_3)_3SiO)_{0.5}$ "M" units, $(CH_3)_2SiO$ "D" units, $(CH_3)SiO_{1.5}$ "T" units, $SiO_2$ "Q" units, and mixtures thereof.

3. The composition of claim 2 wherein the organosiloxane resin is comprised of MQ units, wherein the M:Q ratio is from about 0.5:1.0 to about 1.5:1.0.

4. The composition of claim 1 wherein the organosiloxane resin is present in the composition at a level of from about 5% to about 70%.

5. The composition of claim 1 wherein the volatile carrier is selected from the group consisting of hydrocarbon oils, volatile silicones, non-hydrocarbon solvents, and mixtures thereof.

6. The composition of claim 5 wherein the volatile carrier is selected from the group consisting of isododecane, butanone, ethyl acetate, propyl acetate, methyl nonafluoroisobutyl ether, methyl nonafluorobutyl ether and mixtures thereof.

7. The composition according to claim 1 wherein the pigment is selected from the group consisting of titianium dioxide, bismuth oxychloride, zinc oxide, and mixtures thereof.

8. The composition of claim 7 wherein the pigment comprises from about 0.05% to about 20% of the composition.

9. The composition of claim 1 additionally comprising an teeth color modifying substance selected from the group consisting peroxides, metal chlorites, perborates, percarbonates, peroxyacids, persulfates, and mixtures thereof.

10. The composition of claim 1 wherein the rheology modifier is selected from the group consisting of organo modified clays, silicas, and mixtures thereof.

11. The composition of claim 10 wherein the rheology modifier is present in the composition at a level of from about 0.1% to about 30%.

12. A composition for delivering an oral care substance to the oral cavity, comprising:
   a. an organosiloxane resin;
   b. a fluid diorganopolysiloxane-based polymer;
   c. a volatile carrier capable of solublizing the organosiloxane resin and the fluid diorganopolysiloxane polymer;
   d. a rheology modifying agent; and
   e. at least one oral cam substance comprising particles suitable for modifying the color of the teeth and providing an appearance benefit to the teeth when the composition containing such particles is applied to the teeth surfaces,
wherein the particles are pigments selected from the group consisting of talc, mica, magnesium carbonate, calcium carbonate, magnesium silicate, aluminum magnesium silicate, silica, titanium dioxide, zinc oxide, red iron oxide, yellow iron oxide, black iron oxide, ultramarine, nylon powder, polyethylene powder, methacrylate powder, polystyrene powder, silk powder, crystalline cellulose, starch, titanated mica, iron oxide titanated mica, bismuth oxychloride, and mixtures thereof.

13. The composition of claim 12 wherein the fluid diorganopolysiloxane polymer comprises repeating units of the formula $(R_2SiO)_n$, where R is a monovalent radical group containing from 1 to 6 carbon atoms.

14. The composition of claim 13 wherein said radical group is selected from the group consisting of methyl, ethyl, propyl, isopropyl, butyl, isobutyl, t-butyl, amyl, hexyl, vinyl, allyl, cyclohexyl, amino alkyl, phenyl, fluoroalkyl and mixtures thereof.

15. The composition of claim 14 wherein the fluid diorganopolysiloxane polymer is terminated by triorganosilyl groups of the formula $(R'_3Si)$ where R' is a monovalent radical selected from the group consisting of a radical containing from 1 to 6 carbon atoms, hydroxyl groups, alkoxyl groups and mixtures thereof.

16. The composition of claim 12 wherein the fluid diorganopolysiloxane-based polymer is poly (dimethylsiloxane) or polyalkylene oxide modified poly (dimethylsiloxane).

17. The composition of claim 12 wherein the volatile carrier is selected from the group consisting of hydrocarbon oils, volatile silicones, non-hydrocarbon solvents and mixtures thereof.

18. The composition of claim 17 wherein the volatile carrier is selected from the group consisting of isododecane, butanone, ethyl acetate, propyl acetate, methyl nonafluoroisobutyl ether, methyl nonafluorobutyl ether, and mixtures thereof.

19. The composition of claim 12 wherein the oral care substance includes at least one oral care active selected from the group consisting of an anti-tartar agent, a fluoride ion source, an anti-microbial agent, an anti-inflammatory agent, one or more nutrients, a mouth and throat product, an antioxidant, an H2 antagonist, an analgesic active, flavoring agents, sweetening agents, xylitol, chelants, anti-viral agents and mixtures thereof.

20. The composition of claim 19 wherein the pigment comprises from about 0.05% to about 20% of the composition.

21. The composition of claim 20 additionally comprising a teeth color modifying substance selected from the group consisting peroxides, metal chlorites, perborates, percarbonates, peroxyacids, persulfates and mixtures thereof.

22. The composition of claim 12 wherein the rheology modifier is selected from the group consisting of organo modified clays, silicas, and mixtures thereof.

23. The composition of claim 22 wherein the rheology modifier is present in the composition at a level of from about 0.1% to about 30%.

24. A method for delivering an oral care substance to at least one surface of die oral cavity, comprising the steps of: (1) applying the composition of claim 1 or claim 12 to the surface(s) of the oral cavity; (2) allowing the composition to form a film on the surface(s) of the oral cavity.

25. The method of claim 24 wherein the composition comprises a teeth color modifying substance and the oral cavity surface to which the composition is applied is the enamel of the teeth.

* * * * *

UNITED STATES PATENT AND TRADEMARK OFFICE
CERTIFICATE OF CORRECTION

PATENT NO.    : 6,569,408 B1
DATED         : May 27, 2003
INVENTOR(S)   : Yue et al.

It is certified that error appears in the above-identified patent and that said Letters Patent is hereby corrected as shown below:

Column 12,
Line 38, delete "144.5" and insert -- 44.5 --

Column 15,
Line 34, delete "Altematively" and insert -- Alternatively --

Signed and Sealed this

Ninth Day of December, 2003

JAMES E. ROGAN
*Director of the United States Patent and Trademark Office*